US00PP17324P2

(12) United States Plant Patent
Ren

(10) Patent No.: US PP17,324 P2
(45) Date of Patent: Dec. 26, 2006

(54) ***CALIBRACHOA* PLANT NAMED 'BALCABCHER'**

(50) Latin Name: *Calibrachoa×hybrida*
Varietal Denomination: Balcabcher

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/301,496

(22) Filed: Dec. 13, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—Audrey Charles

(57) ABSTRACT

A new and distinct cultivar of *Calibrachoa* plant named 'Balcabcher' characterized by its deep cherry rose-colored flowers, medium green-colored foliage, and moderately vigorous, mounded-trailing growth habit.

1 Drawing Sheet

Latin name of genus and species of plant claimed: *Calibrachoa×hybrida.*
Variety denomination: 'Balcabcher'.

BACKGROUND OF THE INVENTION

The present invention relates to a new and distinct cultivar of *Calibrachoa* plant botanically known as *Calibrachoa× hybrida* and hereinafter referred to by the cultivar name 'Balcabcher'.

The new cultivar originated in a controlled breeding program in Elburn, Ill. during November 2002. The objective of the breeding program was the development of *Calibrachoa* cultivars with attractive flower coloration, medium green-colored foliage, and moderately vigorous, mounded-trailing growth habit.

The female (seed) parent of the new cultivar was the proprietary *Calibrachoa×hybrida* breeding selection designated 1031-3, not patented, characterized by its cherry red-colored flowers, dark green-colored foliage, and semi-upright growth habit. The male (pollen) parent of the new cultivar was a pollen mix of 13 proprietary *Calibrachoa× hybrida* breeding selections 1015-1m-1a, 1015-1m-3b, 1023-2, 1031-3, 1032-4, 1036-1, 2045-6, 2049-1, 2057-1, 2058-1, 2058-5, 2061-1, and 2074-1a, not patented, characterized respectively by the following colors dark blue, magenta pink, rose, red, cherry, light blue, bright pink, dark purple, bright pink, yellow, white, blue, and dark rose. The new *Calibrachoa* was discovered and selected by the inventor as a single flowering plant within the progeny of the above stated cross-pollination during June 2003 in a controlled environment at Elburn, Ill.

Asexual reproduction of the new cultivar by terminal stem cuttings since June 2003 at Elburn, Ill. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balcabcher' as a new and distinct cultivar of *Calbrachoa* plant:

1. Deep cherry rose-colored flowers;
2. Medium green-colored foliage; and
3. Moderately vigorous, mounded-trailing growth habit.

Plants of the new cultivar differ from plants of the female parent primarily in flower color, foliage color, and growth habit.

Of the many commercially available *Calibrachoa* cultivars known to the inventor, the most similar in comparison to the new cultivar is 'Sunbelre', U.S. Plant Pat. No. 14,756. However, in side by side comparisons, plants of the new cultivar differ from plants of 'Sunbelre' in the following characteristics:

1. Plants of the new cultivar are shorter than plants of 'Sunbelre'; and
2. Plants of the new cultivar have smaller leaves than plants of 'Sunbelre'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcabcher'. The plants were grown in 10 cm pots for 11 weeks in a greenhouse at West Chicago, Ill.

DETAILED BOTANICAL DESCRIPTION

Figure 1:
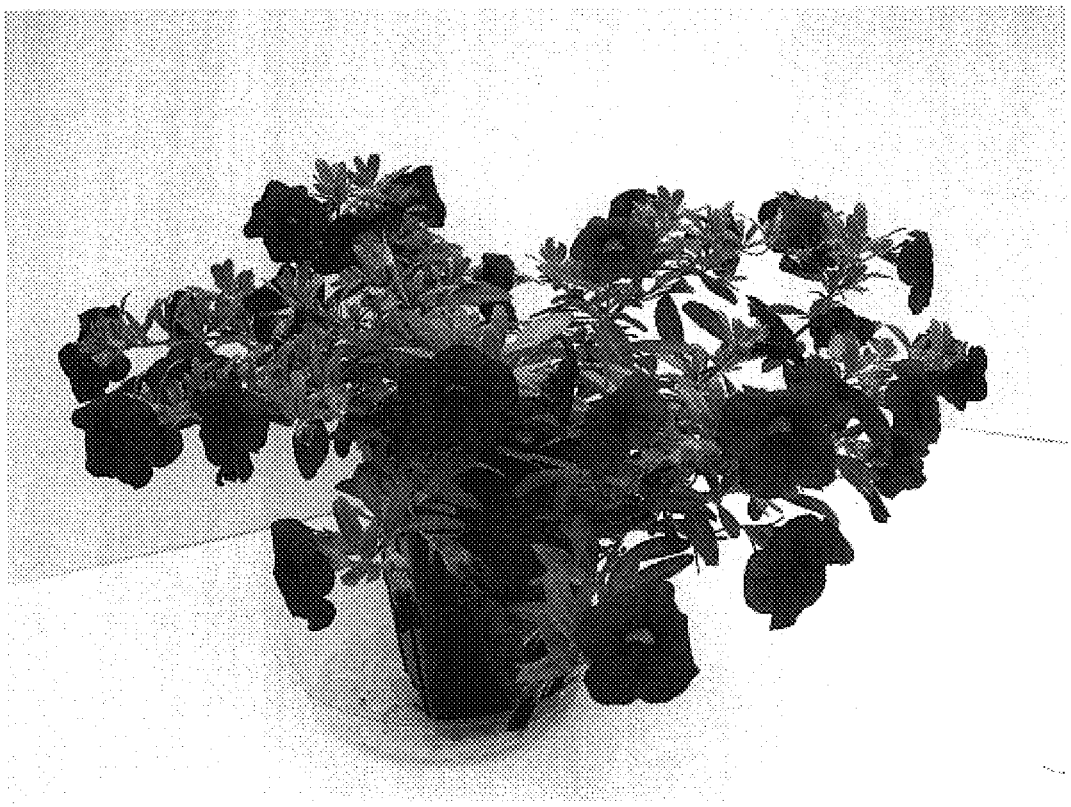
FIG. 1 illustrates a side view of the overall growth and flowering habit of 'Balcabcher'.
Figure 2:
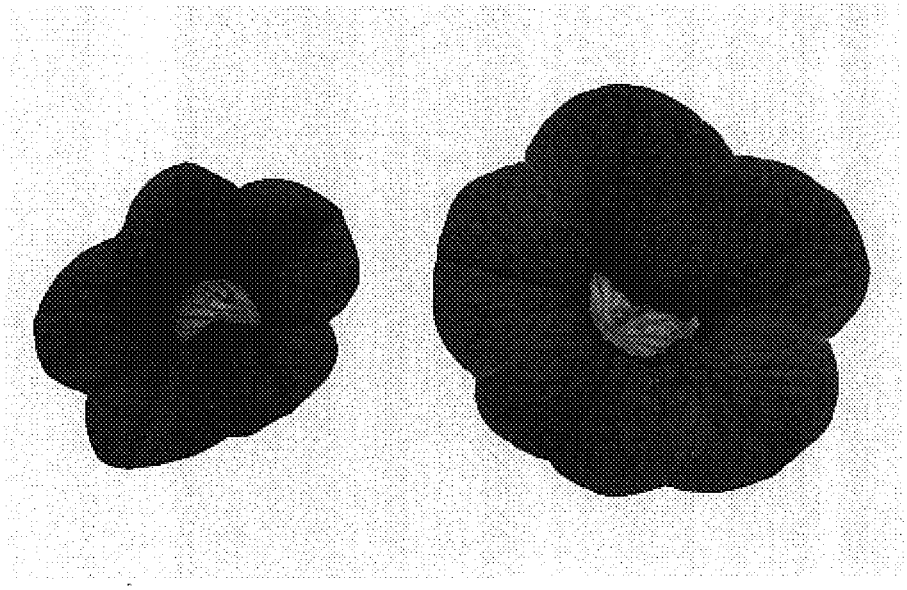
FIG. 2 illustrates a close-up view of a fully open individual flower of 'Balcabcher'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 31, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 11 weeks utilizing a soilless growth medium. Greenhouse temperatures were maintained at approximately 70° F. to 75° F. (21° C. to 24° C.) during the day and approximately 50° F. to 58° F. (10° C. to 14° C.) during the night. Greenhouse light levels of 5,000–8,000 footcandles were maintained during the day.

Botanical classification: *Calibrachoa×hybrida* cultivar Balcabcher.

Parentage:

*Female parent.*—Proprietary *Calibrachoa×hybrida* breeding selection designated 1031-3, not patented.

*Male parent.*—Pollen mix of proprietary *Calibrachoa×hybrida* breeding selections, 1015-1m-1a, 1015-1m-3b, 1023-2, 1031-3, 1032-4, 1036-1, 2045-6, 2049-1, 2057-1, 2058-1, 2058-5, 2061-1, and 2074-1a, not patented.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Crop time.*—Approximately 6 to 9 weeks from a rooted cutting.

*Growth habit and general appearance.*—Moderately vigorous, mounded-trailing.

*Size.*—Height from soil level to top of plant plane: Approximately 12.1 cm. Width: Approximately 47.2 cm.

*Branching habit.*—Freely basal branching. Approximately 8 main branches per plant, with lateral branches forming at very node.

*Branch.*—Strength: Moderate. Length: Approximately 23.1 cm. Diameter: Approximately 2.7 mm. Texture: Densely pubescent. Color of young stem: 144C with overlay of 187A. Color of mature stem: 197C. Internode length at center of branch: Approximately 1.4 cm.

*Foliage.*—Number of leaves per main branch: Approximately 25. Fragrance: None. Form: Simple. Arrangement on flowering stem: Opposite. Aspect: At acute angle to stem with tip downward turning. Shape: Elliptic. Margin: Entire. Apex: Obtuse. Base: Attenuate. Venation pattern: Pinnate. Length of mature leaf: Approximately 3.3 cm. Width of mature leaf: Approximately 1.1 cm. Texture of upper and lower surfaces: Hirsuite. Color of upper surface of young foliage: 144B with venation of 144C. Color of lower surface of young foliage: Lighter than 143C with venation of 144C. Color of upper surface of mature foliage: 137B with venation of 144C. Color of lower surface of mature foliage: 138B with venation of 144C. Petiole length: Approximately 3.3 mm. Petiole diameter: Approximately 1.9 mm. Petiole texture: Hirsuite. Petiole color: 145A.

Flowering description:

*Flowering habit.*—'Balcabcher' is freely flowering under outdoor growing conditions with substantially continuous blooming from spring through autumn and year round in greenhouse environment.

*Time to first flower.*—Approximately 10.5 weeks from sticking of unrooted cutting.

*Lastingness of individual bloom.*—Approximately 5 days.

Flower description:

*Type.*—Simple, salverform. Quantity per plant: Approximately 53.

*Bud rate of opening.*—Generally takes 4 to 6 days for bud to progress from first color to fully open flower.

*Bud just before opening.*—Number of buds per plant: 26.0. Shape: Oblong. Length: Approximately 2.5 cm. Diameter: Approximately 7.9 mm. Texture: Puberulent. Color: Petals closest to 70A and corolla tube 5D with venation of N186C.

*Corolla.*—Diameter: Approximately 3.7 cm.

*Petals.*—Quantity: 5, fused to form a tube. Shape: Obovate. Apex: Obtuse. Margin: Entire. Texture of upper surface: Glabrous. Texture of lower surface: Glabrous and densely pubescent along veins. Petal length from throat: Approximately 1.8 cm. Petal length of free portion: Approximately 7.1 mm. Petal width: Approximately 1.6 cm. Color of upper surface when fully open: Background darker than N74A at the margin and 61A in center, with venation throughout of 59B, giving flowers a deep red-purple coloration. Color of lower surface when fully open: Background of 71C with midvein of 79A and other veins of 79B.

*Corolla tube.*—Length: Approximately 1.8 cm. Diameter at distal end: Approximately 1.1 cm. Diameter at proximal end: Approximately 2.0 mm. Texture of inner surface: Glabrous. Texture of outer surface: Pubescent. Color of inner surface: 13B with venation closest to 59B and midveins of 187A. Color of outer surface: 15D with venation of N79A.

*Peduncle.*—Strength: Moderate. Aspect: Acute angle to stem. Length: Approximately 1.7 cm. Diameter: Approximately 1.0 mm. Texture: Densely pubescent. Color: 145A.

*Sepals.*—Quantity per flower: 5 fused along lower half. Shape: Lanceolate. Apex: Acute. Sepal length: Approximately 1.4 cm. Sepal width: Approximately 3.4 mm. Texture of upper and lower surfaces: Densely pubescent. Color of upper and lower surfaces: 144B at apex with 144D at base.

*Reproductive organs.*—Androecium: Stamen quantity: 5 fused to inside of corolla tube. Stamen length: Approximately 2.1 cm. Filament length of free portion: Approximately 7.5 mm. Filament color: 145C. Anther shape: 2 parted, oval. Anther length: Approximately 0.8 mm. Anther color: 8B. Pollen amount: Abundant. Pollen color: 8A. Gynoecium: Pistil quantity: One per flower. Pistil length: Approximately 1.4 cm. Stigma shape: Funnel. Stigma length: Approximately 1.0 mm. Stigma color: N144C. Style length: Approximately 1.1 cm. Style color: N144D. Ovary diameter: Approximately 2.0 mm. Ovary color: N144C.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcabcher', substantially as herein shown and described.

* * * * *